(12) United States Patent
Kimura

(10) Patent No.: US 6,231,835 B1
(45) Date of Patent: May 15, 2001

(54) AEROSOL PREPARATION FOR SKIN COOLING

(75) Inventor: Fuminori Kimura, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/445,563

(22) PCT Filed: Jun. 11, 1998

(86) PCT No.: PCT/JP98/02576

§ 371 Date: Dec. 9, 1999

§ 102(e) Date: Dec. 9, 1999

(87) PCT Pub. No.: WO98/56350

PCT Pub. Date: Dec. 17, 1998

(30) Foreign Application Priority Data

Jun. 13, 1997 (JP) ................................................ 9-156402

(51) Int. Cl.$^7$ ...................................................... A61K 9/12
(52) U.S. Cl. ........................... 424/45; 424/47; 424/78.02; 514/945; 514/817
(58) Field of Search ........................... 424/45, 47, 78.02; 514/945, 817

(56) References Cited

U.S. PATENT DOCUMENTS 5,397,564   3/1995   Seiki et al. ............................ 424/45

FOREIGN PATENT DOCUMENTS

| 2-255890 | 10/1990 | (JP) | ................................. | C09K/3/30 |
| 4-103526 | 4/1992 | (JP) | ................................. | A61K/9/12 |
| 8-99868 | 4/1996 | (JP) | ................................. | A61K/9/12 |
| 9-110677 | 4/1996 | (JP) | ................................. | A61K/9/12 |
| 90/11068 | 10/1990 | (WO) | ................................. | A61K/9/12 |
| 97/05858 | 2/1997 | (WO) | ......................... | A61K/31/045 |

*Primary Examiner*—Raj Bawa
(74) *Attorney, Agent, or Firm*—Sughrue, Mion, Zinn, Macpeak & Seas, PLLC

(57) ABSTRACT

An aerosol preparation for skin-cooling which coagulates sherbet-like on the applied site when sprayed, comprising a liquefied gas and a concentrate containing a $C_{1-3}$ lower alcohol and a $C_{10-22}$ straight chain monocarboxylic acid can contain drugs labile in water of which the incorporation has been difficult in the previous aerosol preparations, gives a good feeling when used, and have a durable cooling effect. Accordingly, it is effective on quick calming the pain caused by contusion, sprain, muscular fatigue, etc. or the itch caused by athlete's foot, insect bite, etc.

7 Claims, No Drawings

AEROSOL PREPARATION FOR SKIN COOLING

TECHNICAL FIELD

The present invention relates to an aerosol preparation which has an enhanced cooling effect by coagulating sherbet-like when sprayed.

BACKGROUND ART

Up to now, jel preparations or aerosol preparations have been ordinarily used for calming the pain caused by contusion, sprain, muscular fatigue, etc. or the itch caused by athlete's foot, insect bite, etc. However, the gel preparations are inferior in the immediate effect, and the aerosol preparations usually used do not have a durable effect.

Generally, it is effective to cool the affected site for calming pain or itch. As examples of aerosol preparations having a durable cooling effect for the purpose, the specifications of WO90/11068 and Japanese Patent Kokai 4-103526 disclose aerosol preparations which form a sherbet-like foam gel when sprayed. However, these aerosol preparations require complicated procedures for the productions thereof. Furthermore, since it is essential to contain water in the concentrate of these aerosol preparations, it is difficult to contain drugs labile in water or highly lipophilic drugs. In addition, these aerosol preparations lack a satisfactory feeling when used.

An object of the present invention is to provide an aerosol preparation which solves inconvenient points of the previous techniques, and has a strong and durable skin-cooling ability when sprayed.

DISCLOSURE OF THE INVENTION

As a result of various researches in order to meet the above-mentioned purposes, the present inventors have found that an aerosol preparation containing a lower alcohol, a straight chain monocarboxylic acid and a liquefied gas has a durable cooling effect by coagulating sherbet-like on the applied site when sprayed, and gives a remarkably superior feeling when used, thus the present invention has been accomplished.

That is, the present invention is directed to an aerosol preparation for skin-cooling which comprises a concentrate containing a $C_{1-3}$ lower alcohol and a $C_{10-22}$ straight chain monocarboxylic acid and a liquefied gas, and which coagulates sherbet-like on the applied site when sprayed.

There have not been known up to now any aerosol preparations for skin-cooling which have a cooling effect caused by containing the straight chain monocarboxylic acid in the preparation. Any previously known aerosol preparations having a durable skin-cooling effect coagulate by freezing water which is contained therein when sprayed, thereby sustain the cooling effect, while, the aerosol preparation of the present invention does not always necessarily contain water, and is characterized by its coagulation under the entirely novel conditions when sprayed.

In the present invention, the term "sherbet-like" refers to a state of the aerosol preparation which has coagulated partially on the applied site by the cooling ability driven by the vaporization of the liquefied gas when sprayed, and specifically, refers to a state of the interminglement of a liquid with a minute crystalline coagulum on the applied site. In the present invention, when sprayed, the lower alcohol as a liquid and the straight chain monocarboxylic acid as a fine crystalline coagulum are intermingled, as the result, the durable cooling effect is assumed to occur.

In the present invention, the $C_{1-3}$ lower alcohol refers to a straight or branched chain alcohol, specific examples thereof are methanol, ethanol, denatured ethanol, propanol and isopropanol, and preferably ethanol and isopropanol. The amount of the lower alcohol is preferably from 6 to 99% by weight, more preferably 10 to 95% by weight, and most preferably 30 to 90% by weight based on the concentrate. When the amount of the lower alcohol is less than 6% by weight based on the concentrate, the concentrate may not be easily intermingled homogeneously with the propellant, while, when the amount of the lower alcohol is more than 99% by weight, the durability of the cooling effect may be deteriorated.

In the present invention, the $C_{10-22}$ straight chain monocarboxylic acid includes preferably lauric acid, myristic acid, palmitic acid, stearic acid or behenic acid, and most preferably stearic acid.

The amount of the straight chain monocarboxylic acid ranges preferably from 1 to 28% by weight, more preferably from 1.5 to 20% by weight, and most preferably from 2 to 15% by weight based on the concentrate. When the amount of the straight chain monocarboxylic acid is less than 1% by weight based on the concentrate, the aerosol preparation cannot easily coagulate when sprayed, thereby a durable cold feeling may be deteriorated, while, when it is more than 28% by weight, the straight chain monocarboxylic acid cannot be easily dissolved, thereby the production procedure may be complicated.

In the present invention, unless a completely homogenous system exists when the straight chain monocarboxylic acid, the lower alcohol and the liquefied gas are mixed, the effect of the present invention cannot be obtained. Accordingly, when the solubility of the straight chain monocarboxylic acid is insufficient, it is possible to contain other solvents, dissolving assistants, surface active agents or the like.

The liquefied gas includes ones which can be used as propellants in ordinary aerosol preparations, and preferable examples thereof are dimethyl ether, n-butane, i-butane, propane and liquefied petroleum gas, and they can be used alone or in admixture. Dimethyl ether, n-butane and i-butane are especially preferred.

The amount of the liquefied gas ranges preferably from 0.5 to 20 parts by weight, and more preferably from 1 to 9 parts by weight based on one part by weight of the concentrate. When the amount of the liquefied gas is less than 0.5 part by weight based on one part by weight of the concentrate, the cold feeling by the aerosol preparation may be deteriorated, thereby the calming effect on pain or itch may be deteriorated, while, when the amount of the liquefied gas is more than 20 parts by weight, the aerosol preparation may not form a sherbet-like solid when sprayed, thereby the durable cooling effect may not be easily obtainable.

The aerosol preparation of the present invention can be prepared by dissolving the lower alcohol and the straight chain monocarboxylic acid so as to give a homogeneous system, and if desired, further incorporating such other components that do not destroy the homogeneous system into the concentrate, and filling the resulting concentrate together with the liquefied gas into an aerosol container. Examples of the aerosol container include containers made of metals or plastics as used usually. In view of the durability of the cooling effect, it is preferable to contain a suitable amount of water as such another component that does not destroy the homogeneous system. In case of combination of water with the concentrate, not more than 90% by weight of water can be added based on the total amount of the concentrate, but it is preferable to incorporate 20 to 60% by weight of water into the concentrate in view of an easy recipe of the preparation.

In order to enhance the calming effect on pain and itch on the affected site, it is possible to incorporate drug-effective components such as anti-inflammatory and analgesic agents, antipruritics, antifungal agents, vasodilators, antihistaminic agents, local anesthetics, antibiotics, antiphlogistics, keratolytics, refrigerants and the like into the aerosol preparation of the present invention. In particular, it is possible to incorporate drugs labile in water or highly lipophilic drugs into the aerosol preparation of the present invention. The amount of the drug-effective component can be varied depending on the kind of the component, but usually it ranges from 0.001 to 10% by weight based on the total amount of the preparation.

The aerosol preparation of the present invention can contain, if necessary, any additives which can be used for ordinary aerosol preparations, for example, anti-oxidants, percutaneous absorption promoters, humectants, emulsifying adjuncts, gelling agents, thickening agents, perfumes, dyes and the like.

BEST MODE FOR CARRYING OUT THE INVENTION

The present invention is illustrated in more detail by the following examples and test examples.

EXAMPLE 1

3.11 Parts by weight of stearic acid and 21.41 parts by weight of ethanol were mixed to give a concentrate. The concentrate was filled into a pressure-resistant container, a valve was attached thereto, and 0.08 part by weight of propane, 2.11 parts by weight of n-butane, 1.07 parts by weight of i-butane and 72.22 parts by weight of dimethyl ether were filled, thereby there was obtained an aerosol preparation.

EXAMPLE 2

0.31 Part by weight of indomethacin, 4.11 parts by weight of Macrogol 400, 1.23 parts by weight of stearic acid, 1.23 parts by weight of polyoxyethylene cetyl ether, 16.47 parts by weight of denatured ethanol and 13.39 parts by weight of purified water were mixed, stirred and dissolved homogeneously to give a concentrate. The concentrate was filled into a pressure-resistant container, a valve was attached thereto, and 63.26 parts by weight of dimethyl ether was filled, thereby there was obtained an aerosol preparation.

EXAMPLE 3

0.18 Part by weight of piroxicam, 1.76 parts by weight of Macrogol 400, 0.7 part by weight of glycerol, 0.53 part by weight of stearic acid, 0.53 part by weight of palmitic acid, 0.7 part by weight of polyoxyethylene stearyl ether, 0.35 part by weight of polyoxyethylene hydrogenated castor oil, 16.85 parts by weight of denatured ethanol and 8.74 parts by weight of purified water were mixed, stirred and dissolved homogeneously to give a concentrate. The concentrate was filled into a pressure-resistant container, a valve was attached thereto, and 69.49 parts by weight of dimethyl ether was filled, thereby there was obtained an aerosol preparation.

EXAMPLE 4

0.35 Parts by weight of miconazole nitrate, 1.76 parts by weight of diisopropyl adipate, 1.06 parts by weight of isopropyl myristate, 0.7 part by weight of glycerol, 0.35 part by weight of polyethylene glycol distearate, 0.35 part by weight of decaglyceryl distearate, 0.35 part by weight of polyoxyethyleneglycerol monostearate, 0.7 part by weight of myristic acid, 0.35 part by weight of stearic acid, 0.7 part by weight of behenic acid and 16.83 parts by weight of ethanol were mixed, stirred and dissolved homogeneously to give a concentrate. The concentrate was filled into a pressure-resistant container, a valve was attached thereto, and 0.86 part by weight of propane, 4.22 parts by weight of n-butane, 2.14 parts by weight of i-butane and 69.32 parts by weight of dimethyl ether were filled, thereby there was obtained an aerosol preparation.

Comparative Example 1

Following the same method as in Example 1 using the formulation of Example 1 in which the stearic acid was replaced with ethanol, there was obtained an aerosol preparation.

Comparative Example 2

Following the same method as in Example 2 using the formulation of Example 2 in which the polyoxyethylene cetyl ether and stearic acid were replaced with denatured ethanol and purified water, respectively, there was obtained an aerosol preparation for comparison.

Comparative Example 3

0.36 part by weight of indomethacin, 1.79 parts by weight of diisopropyl adipate, 1.07 parts by weight of isopropyl myristate, 0.71 part by weight of glycerol, 17.06 parts by weight of denatured ethanol and 8.27 parts by weight of purified water were mixed, stirred and dissolved homogeneously to give a concentrate. The concentrate was filled into a pressure-resistant container, a valve was attached thereto, and 70.74 parts by weight of dimethyl ether was filled, thereby there was obtained an aerosol preparation for comparison.

Comparative Example 4

By basically following the method for producing sherbet-like aerosol preparation as described in Example 1 of Japanese Patent Kokai 4-103526, there was obtained an aerosol preparation.

That is, 0.31 part by weight of indomethacin, 4.07 parts by weight of diisopropyl adipate, 1.22 parts by weight of polyoxyethylene sorbitan monostearate, 0.81 part by weight of polyoxyethylene sorbitan tristearate and 1.22 parts by weight of sorbitan monostearate were dissolved under heating, and 15.94 parts by weight of hot purified water was added thereto and mixed thoroughly. After further cooling with stirring, 14.23 parts by weight of denatured ethanol was added thereto and dispersed homogeneously to give a concentrate. The concentrate was filled into a pressure-resistant container, a valve was attached thereto, and 62.20 parts by weight of dimethyl ether was filled, thereby there was obtained an aerosol preparation.

Test Example 1

A sheet with which a thermocouple sensor was fixed using adhesive tapes was spread on a thermostat water bath controlled at 33° C. The aerosol preparations obtained in Examples 1 to 4 and Comparative Examples 1 to 4 were each sprayed on the thermocouple sensor for 3 seconds. The properties of the sprayed aerosol preparations were observed, and the values that the thermocouple sensor indicated were recorded with time. Results are shown in Table 1.

TABLE 1

| | Sprayed aerosol preparation | Change of the temperature of thermocouple sensor (° C.) | | | | | | | |
|---|---|---|---|---|---|---|---|---|---|
| | | before spray | 15 sec. | 30 sec. | 45 sec. | 60 sec. | 90 sec. | 120 sec. | 180 sec. |
| Example 1 | ○ | 33.1 | 14.9 | 15.7 | 17.1 | 20.2 | 22.6 | 30.0 | 31.4 |
| Example 2 | ○ | 33.0 | 13.9 | 14.1 | 17.9 | 21.4 | 24.1 | 30.9 | 32.0 |
| Example 3 | ○ | 33.0 | 14.3 | 14.9 | 16.7 | 21.0 | 23.2 | 31.2 | 32.6 |
| Example 4 | ○ | 33.1 | 14.4 | 14.9 | 15.1 | 20.8 | 21.7 | 29.9 | 32.0 |
| Comparative Example 1 | X | 33.1 | 22.8 | 31.9 | 32.4 | 32.6 | 32.8 | 32.9 | 33.0 |
| Comparative Example 2 | X | 33.0 | 24.0 | 30.8 | 32.5 | 32.5 | 32.6 | 32.8 | 33.0 |
| Comparative Example 3 | X | 33.0 | 24.9 | 31.7 | 32.1 | 32.5 | 32.8 | 32.9 | 32.9 |
| Comparative Example 4 | ○ | 33.0 | 15.6 | 15.5 | 19.2 | 23.4 | 31.2 | 31.3 | 33.0 |

○ indicates that the aerosol preparation coagulated sherbet-like when sprayed.
X indicates that the aerosol preparation did not coagulate sherbet-like when sprayed.

Table 1 indicates that the aerosol preparations of Examples 1 to 4 and Comparative Example 4 coagulated each sherbet-like when sprayed, but those of Comparative Examples 1 to 3 did not form any sherbet-like coagulum. It also demonstrates that in the change of temperature on the thermocouple sensor, the temperatures by the aerosol preparations of Comparative Examples 1 to 3 reached 30° C. or higher at 30 seconds after spraying and were returned to the original temperature at 45 seconds, on the contrary, the aerosol preparations of Examples 1 to 4 and Comparative Example 4 had a durable cooling effect.

Test Example 2

Thirty subjects had a feeling-at-the-time-of-use test of the aerosol preparations of Example 4 and Comparative Example 4, both of which have relatively similar cooling effect. The subjects had a choice from the following three, that is, the preparation which gives a good feeling when used is ① Example 4, ② Comparative Example 4 or ③ similar each other. As a result, ① was chosen by 27 subjects, ② 0, and ③ 1.

From the results of Test example 2, it was confirmed that the aerosol preparation of the present invention is better than the previous sherbet-like aerosol preparation in a feeling when used.

INDUSTRIAL APPLICABILITY

The present invention makes it possible to provide an aerosol preparation which gives a superior feeling when used, and has a durable cooling effect for the long period of time. Furthermore, the present invention makes it possible to provide an aerosol preparation for skin-cooling containing drugs labile in water of which the incorporation has been difficult in the past.

What is claimed is:

1. An aerosol preparation for skin-cooling, comprising:
   (a) a concentrate containing (i) 6 to 99% by weight of a $C_{1-3}$ lower alcohol selected from the group consisting of methanol, ethanol, denatured ethanol, propanol, isopropanol and a mixture thereof and (ii) 1 to 28% by weight of a $C_{10-22}$ straight chain monocarboxylic acid, and
   (b) 0.5 to 20 parts by weight of a liquefied gas selected from the group consisting of dimethyl ether, n-butane, i-butane, propane and a liquefied petroleum gas and a mixture thereof based on one part by weight of the concentrate.

2. An aerosol preparation for skin-cooling, comprising:
   (a) a concentrate containing (i) 6 to 99% by weight of a $C_{1-3}$ lower alcohol selected from the group consisting of ethanol, isopropanol and a mixture thereof and (ii) 1 to 28% by weight of a $C_{10-22}$ straight chain monocarboxylic acid, and
   (b) 0.5 to 20 parts by weight of a liquefied gas selected from the group consisting of dimethyl ether, n-butane, i-butane, propane and a liquefied petroleum gas and a mixture thereof based on one part by weight of the concentrate.

3. The aerosol preparation for skin-cooling according to claim 1 or 2 wherein the $C_{10-22}$ straight chain monocarboxylic acid is selected from the group consisting of lauric acid, myristic acid, palmitic acid, stearic acid, behenic acid and a mixture thereof.

4. The aerosol preparation for skin-cooling according to claim 1 or 2 wherein the $C_{10-22}$ straight chain monocarboxylic acid is stearic acid.

5. The aerosol preparation for skin-cooling according to claim 1 or 2 wherein the concentrate contains water in an amount of 20 to 60% by weight based on the concentrate.

6. The aerosol preparation for skin-cooling according to claim 3 wherein the concentrate contains water in an amount of 20 to 60% by weight based on the concentrate.

7. The aerosol preparation for skin-cooling according to claim 4 wherein the concentrate contains water in an amount of 20 to 60% by weight based on the concentrate.

* * * * *